US012685534B2

(12) United States Patent
Kamikyu et al.

(10) Patent No.: US 12,685,534 B2
(45) Date of Patent: Jul. 21, 2026

(54) TISSUE REINFORCEMENT MATERIAL LOADER AND TISSUE REINFORCEMENT MATERIAL LOADING KIT

(71) Applicant: GUNZE LIMITED, Ayabe (JP)

(72) Inventors: Keisuke Kamikyu, Kyoto (JP); Masayuki Funaoka, Kyoto (JP)

(73) Assignee: Gunze Limited, Kyoto (JP)

( * ) Notice: Subject to any disclaimer, the term of this patent is extended or adjusted under 35 U.S.C. 154(b) by 4 days.

(21) Appl. No.: 19/101,478

(22) PCT Filed: Aug. 8, 2023

(86) PCT No.: PCT/JP2023/028938
§ 371 (c)(1),
(2) Date: Feb. 5, 2025

(87) PCT Pub. No.: WO2024/034611
PCT Pub. Date: Feb. 15, 2024

(65) Prior Publication Data
US 2026/0041427 A1 Feb. 12, 2026

(30) Foreign Application Priority Data

Aug. 10, 2022 (JP) .................................. 2022-128133

(51) Int. Cl.
*A61B 17/072* (2006.01)
*A61L 31/04* (2006.01)
*A61B 17/00* (2006.01)

(52) U.S. Cl.
CPC ...... *A61B 17/07292* (2013.01); *A61L 31/042* (2013.01); *A61L 31/048* (2013.01); *A61B 2017/00951* (2013.01)

(58) Field of Classification Search
CPC A61B 17/07292; A61L 31/042; A61L 31/048
(Continued)

(56) References Cited

U.S. PATENT DOCUMENTS 5,814,057 A 9/1998 Oi et al.
6,063,097 A 5/2000 Oi et al.
(Continued)

FOREIGN PATENT DOCUMENTS

CN 106572856 4/2017
CN 107582122 1/2018
(Continued)

*Primary Examiner* — Nathaniel C Chukwurah
(74) *Attorney, Agent, or Firm* — HSML P.C.

(57) ABSTRACT

The present invention aims to provide a tissue reinforcement material applicator that enables quick, precise, and easy application of a stick-on tissue reinforcement material to a surgical stapler with less application failure, and a tissue reinforcement material application kit including the tissue reinforcement material applicator. Provided is tissue reinforcement material applicator for securing a stick-on tissue reinforcement material to a surgical stapler, the tissue reinforcement material applicator including a plate-shaped member, the tissue reinforcement material applicator having recesses opposing each other on both surfaces of the plate-shaped member, each recess having a shape corresponding to a shape of a portion of the surgical stapler to which the stick-on tissue reinforcement material is to be applied, each recess being continuous with the same edge of the plate-shaped member, each recess having brush-like protrusions on a bottom surface thereof, each recess having, in a side surface thereof, a securing groove for holding the stick-on tissue reinforcement material therein.

13 Claims, 3 Drawing Sheets

(58) Field of Classification Search
USPC ........................................................ 227/175
See application file for complete search history.

(56) References Cited

U.S. PATENT DOCUMENTS

| | | | |
|---|---|---|---|
| 2005/0070929 A1* | 3/2005 | Dalessandro | .... A61B 17/07207 |
| | | | 606/151 |
| 2007/0049953 A2 | 3/2007 | Shimoji et al. | |
| 2017/0056016 A1* | 3/2017 | Barton | ............. A61B 17/07292 |
| 2018/0008264 A1 | 1/2018 | Kang | |

FOREIGN PATENT DOCUMENTS

| | | |
|---|---|---|
| JP | 8-047526 | 2/1996 |
| JP | 4675237 | 4/2011 |
| JP | 2018-525133 | 9/2018 |
| JP | 2022-516713 | 3/2022 |
| WO | 2015/191279 | 12/2015 |
| WO | 2017/035208 | 3/2017 |
| WO | 2020/136483 | 7/2020 |
| WO | 2022/058908 | 3/2022 |

* cited by examiner

TISSUE REINFORCEMENT MATERIAL LOADER AND TISSUE REINFORCEMENT MATERIAL LOADING KIT

TECHNICAL FIELD

The present invention relates to a tissue reinforcement material applicator that enables quick, precise, and easy application of a stick-on tissue reinforcement material to a surgical stapler with less application failure, and a tissue reinforcement material application kit including the tissue reinforcement material applicator.

BACKGROUND ART

Surgical staplers containing many staples have been used in stapling of tissue. However, use of such devices in a tissue such as the lung may cause an air leak from the stapled portion, and use of them in a fragile tissue may cause damage, rupture, or the like of the tissue.

In order to prevent an air leak, a bodily fluid leak, and tissue damage, bioabsorbable reinforcement materials have been used together with surgical staplers (for example, Patent Literatures 1 and 2). The reinforcement materials of Patent Literatures 1 and 2 have a tubular structure formed by sewing two opposite sides of one bioabsorbable nonwoven fabric sheet together, or by stacking two bioabsorbable nonwoven fabric sheets or one bioabsorbable nonwoven fabric sheet and one stretchable knitted fabric sheet and sewing two opposite sides together. These reinforcement materials are applied to a surgical stapler by inserting the end of the cartridge of the surgical stapler into the tube, and stapled together with tissue for tissue reinforcement. The reinforcement materials have high workability because unnecessary parts can be removed after reinforcement by pulling threads extending from the reinforcement material. Moreover, the reinforcement materials, which are made of bioabsorbable nonwoven fabric, are eventually absorbed in the living body after reinforcement is no longer needed.

CITATION LIST

Patent Literature

Patent Literature 1: JP H08-047526 A
Patent Literature 2: JP 4675237 B

SUMMARY OF INVENTION

Technical Problem

Conventional reinforcement materials used in surgical staplers combine a tissue-reinforcing fabric and a stretchable fabric to form a tubular shape that can adhere closely to the surgical stapler, so as to prevent displacement during operation of the surgical stapler. However, since surgical stapler cartridges come in various sizes, reinforcement materials may not be closely adhered to the surgical stapler and may be displaced depending on the size of the cartridge. Even a reinforcement material fit to the size of the cartridge can be displaced because of gaps near the seams of the fabrics.

In endoscopic surgery using a surgical stapler, multiple tubular ports are placed in the patient's body, through which tools such as an endoscope or a surgical stapler are inserted. When a surgical stapler is inserted into a port, a conventional reinforcement material, which is applied to surround the cartridge of the surgical stapler, may get caught on the port.

In addition, the reinforcement material surrounding the cartridge makes the surgical stapler larger, preventing the surgical stapler from passing through a port unless the port has a diameter larger than the size of the surgical stapler itself. To reduce patients' burden, there is demand for a reinforcement material that can pass through ports of smaller diameters.

In response to this, the Applicant proposed a staple line reinforcement material for surgical staplers that includes a fabric layer containing a bioabsorbable material and a sponge layer containing a water-soluble polymer, wherein the fabric layer and the sponge layer are integrally laminated. Such a staple line reinforcement material for surgical staplers can exhibit adhesion as the sponge layer absorbs moisture, and can be applied to a surgical stapler by bonding it to the cartridge. The material therefore can be used in surgical staplers of various sizes, can easily pass through ports, and is less likely to be displaced in operation of the surgical stapler.

Unfortunately, such a stick-on tissue reinforcement material is more difficult to apply than conventional tubular tissue reinforcement materials because it is immersed in water before applied to the surgical stapler. Moreover, if applied to a position displaced from the intended position, a stick-on tissue reinforcement material needs to be peeled off and then re-applied. There is thus demand for a way to easily and precisely apply a stick-on tissue reinforcement material to a surgical stapler.

In view of the above problems, the present invention aims to provide a tissue reinforcement material applicator that enables quick, precise, and easy application of a stick-on tissue reinforcement material to a surgical stapler with less application failure, and a tissue reinforcement material application kit including the tissue reinforcement material applicator.

Solution to Problem

The present invention encompasses the following disclosures. The present invention is described in detail in the following.

The disclosure 1 relates to a tissue reinforcement material applicator for securing a stick-on tissue reinforcement material to a surgical stapler, the tissue reinforcement material applicator including a plate-shaped member, the tissue reinforcement material applicator having recesses opposing each other on both surfaces of the plate-shaped member, each recess having a shape corresponding to a shape of a portion of the surgical stapler to which the stick-on tissue reinforcement material is to be applied, each recess being continuous with the same edge of the plate-shaped member, each recess having brush-like protrusions on a bottom surface thereof, each recess having, in a side surface thereof, a securing groove for holding the stick-on tissue reinforcement material therein.

The disclosure 2 relates to the tissue reinforcement material applicator according to the disclosure 1, wherein a bottom of the recesses is different in material from another portion.

The disclosure 3 relates to the tissue reinforcement material applicator according to the disclosure 1 or 2, wherein a bottom of the recesses has an opening in a portion that is to contact a tip of the surgical stapler.

The disclosure 4 relates to the tissue reinforcement material applicator according to any one of the disclosures 1 to 3, wherein the brush-like protrusions have a density of 9 protrusions/cm$^2$ or greater and 25 protrusions/cm$^2$ or less.

The disclosure 5 relates to the tissue reinforcement material applicator according to any one of the disclosures 1 to 4, wherein the brush-like protrusions have a length of 0.5 mm or greater and 5 mm or less.

The disclosure 6 relates to the tissue reinforcement material applicator according to any one of the disclosures 1 to 5, wherein the brush-like protrusions become shorter toward ends of the recesses, the ends being on a proximal side of the surgical stapler.

The disclosure 7 relates to the tissue reinforcement material applicator according to any one of the disclosures 1 to 6, wherein each recess becomes wider toward a proximal side of the surgical stapler.

The disclosure 8 relates to the tissue reinforcement material applicator according to any one of the disclosures 1 to 7, including guide walls along both long sides of each recess.

The disclosure 9 relates to the tissue reinforcement material applicator according to the disclosure 8, wherein each guide wall has an end on a proximal side of the surgical stapler, and the end is inclined downward toward the proximal side.

The disclosure 10 relates to the tissue reinforcement material applicator according to any one of the disclosures 1 to 9, including a grip at an end thereof on a distal side of the surgical stapler.

The disclosure 11 relates to the tissue reinforcement material applicator according to the disclosure 10, wherein the grip has a cut-out in a side surface on a side of the recesses.

The disclosure 12 relates to a tissue reinforcement material application kit including: the tissue reinforcement material applicator according to any one of the disclosures 1 to 11; and the stick-on tissue reinforcement material held in the securing grooves of the tissue reinforcement material applicator.

The disclosure 13 relates to the tissue reinforcement material application kit according to the disclosure 12, including a cap at an end thereof on a proximal side of the surgical stapler.

In the following, the tissue reinforcement material applicator of the present invention and a stick-on tissue reinforcement material, for which the tissue reinforcement material is to be used, are described in detail. First, the tissue reinforcement material applicator of the present invention is described in detail below.

The tissue reinforcement material applicator of the present invention is for securing a stick-on tissue reinforcement material to a surgical stapler.

Stick-on tissue reinforcement materials are advantageous over conventional tubular tissue reinforcement materials in that they rarely get caught in a port and thus can be used regardless of the size of the tissue reinforcement material. However, application of a stick-on tissue reinforcement requires bonding it to a predetermined position of a surgical stapler, which makes quick and precise application difficult. The tissue reinforcement material applicator of the present invention enables quick, precise, and easy application of a stick-on tissue reinforcement material to a surgical stapler regardless of the user's skill level.

The tissue reinforcement material applicator of the present invention includes a plate-shaped member, and the tissue reinforcement material applicator has recesses opposing each other on both surfaces of the plate-shaped member.

Providing recesses opposing each other on both surfaces of the plate-shaped member (surfaces perpendicular to the thickness direction of the member) and holding the stick-on tissue reinforcement material in these recesses can improve the handleability of the stick-on tissue reinforcement material during transfer and storage. Moreover, by immersing the stick-on tissue reinforcement material in water or an aqueous solution (hereinafter simply referred to as an aqueous solution) together with the tissue reinforcement material applicator and clamping the recesses between the jaws of the surgical stapler, two pieces of the stick-on tissue reinforcement material can be simultaneously applied to the surgical stapler. Examples of the aqueous solution include sterilized water, saline, and buffer solutions. The "plate-shaped" herein refers to a flat shape having a thickness that can be clamped between the jaws of a surgical stapler.

Each recess has a shape corresponding to the shape of a portion of the surgical stapler to which the stick-on tissue reinforcement material is to be applied, and each recess is continuous with the same edge of the plate-shaped member.

When each recess has a shape corresponding to the shape of a portion of the surgical stapler to which the stick-on tissue reinforcement material is to be applied, the stick-on tissue reinforcement material can be precisely applied to a predetermined position. When the two recesses are continuous with the same edge of the member, the surgical stapler can be inserted into the recesses from the end with which the recesses are continuous. The phrase "continuous with the same edge" refers to a state where the open ends of the two recesses are continuous with the same side surface of the member. The term "side surface" refers to a surface perpendicular to both surfaces of the member.

Each recess has brush-like protrusions on a bottom surface thereof.

When a stick-on tissue reinforcement material is placed in a recess with a flat bottom surface and clamped between the jaws of a surgical stapler, a proximal portion of the surgical stapler contacts the bottom surface of the recess first and gets stuck, which prevents a distal portion of the surgical stapler from making sufficient contact with stick-on tissue reinforcement material, and may stop the clamping. This may result in application failure such as lifting or peeling of the stick-on tissue reinforcement material in the distal portion of the surgical stapler.

In the present invention, each recess has brush-like protrusions (hereinafter also simply referred to as "protrusions") on the bottom surface thereof. When the surgical stapler contacts the protrusions on the bottom of the recesses, the protrusions sequentially bend as clamping proceeds, whereby the bottom of the recesses is inclined. The inclined bottom is thinner on the proximal side of the surgical stapler than on the distal side thereof, and thus does not stop clamping midway, allowing the surgical stapler to sufficiently fit into the recesses to the tip as compared with recesses with flat bottom surfaces. This can reduce or prevent application failure such as lifting or peeling of the stick-on tissue reinforcement material in the distal portion of the surgical stapler. The protrusions each may have a flat or sharp tip, but preferably have a flat tip because then the stick-on tissue reinforcement material can be pressed against the surgical stapler in a larger area and thereby can be easily sufficiently bonded to the surgical stapler. The "bottom" of the recesses herein refers to a portion including the bottom surfaces of the recesses and the protrusions of the recesses.

The protrusions may have any length, but preferably have a length of 0.5 mm or greater, more preferably 1 mm or greater, still more preferably 2 mm or greater while preferably 5 mm or less, more preferably 3 mm or less, still more preferably 2.8 mm or less, so as to enhance the force to press the stick-on tissue reinforcement material against the surgical stapler and reduce or prevent displacement or falling of the stick-on tissue reinforcement material.

Preferably, the brush-like protrusions become shorter toward ends of the recesses, the ends being on a proximal side of the surgical stapler.

When the protrusions become shorter toward the proximal side of the surgical stapler, the bottom of the recesses is inclined even with the protrusions unbent. This allows the surgical stapler to more reliably fit into the recesses to the tip and can reduce application failure. Moreover, the resilience (elasticity) of the protrusions allows the stick-on tissue reinforcement material to more strongly adhere to the surgical stapler to the tip, reducing or preventing lifting and peeling of the stick-on tissue reinforcement material on the tip. The protrusions may become shorter toward the proximal side of the surgical stapler continuously or stepwise. When the protrusions become shorter stepwise, the protrusions preferably become shorter such that each step has the same height.

Herein, "the proximal side of the surgical stapler" refers to a direction closer to a handle of the surgical stapler when the surgical stapler is fitted into the tissue reinforcement material applicator of the present invention, in other words, a direction toward the open ends of the recesses (hereinafter also simply referred to as "proximal side" or "proximal"). Herein, "the distal side of the surgical stapler" refers to a direction opposite to the proximal side of the surgical stapler (hereinafter also simply referred to as "distal side" or "distal").

When the protrusions become shorter toward the proximal side of the surgical stapler, from the standpoint of more tightly fitting the surgical stapler into the recesses, the difference between the maximum length and minimum length of the protrusions is preferably 0.1 mm or greater, more preferably 0.5 mm or greater, while preferably 1.5 mm or less, more preferably 1.0 mm or less.

The protrusions may have any thickness (cross sectional area in a plane direction) that provides the hardness to press the stick-on tissue reinforcement material against the surgical stapler with a sufficient force before inclining while allowing the protrusions to incline as the fitting of the surgical stapler proceeds. To further enhance the force to press the stick-on tissue reinforcement material against the surgical stapler and thereby further reduce or prevent displacement or falling of the stick-on tissue reinforcement material, the protrusions preferably have a thickness of 0.5 $mm^2$ or greater, more preferably 1.0 $mm^2$ or greater while preferably 2.0 $mm^2$ or less, more preferably 1.5 $mm^2$ or less. When the thickness of the protrusions is not constant, the "thickness of the protrusions" refers to the maximum thickness. The "plane direction" herein refers to a surface direction perpendicular to the thickness direction of the tissue reinforcement material applicator.

The protrusions may have any density as long as the protrusions are in such a number that they reliably bend when the surgical stapler is fitted into the recesses. The protrusions preferably have an area density of 9 protrusions/$cm^2$ or greater and 25 protrusions/$cm^2$ or less. When the number of protrusions is set to achieve the area density within the range, the protrusions can reliably bend when the surgical stapler is fitted into the recesses while, before bending, pressing the stick-on tissue reinforcement material into contact with the surgical stapler uniformly in a larger area. The protrusions more preferably have an area density of 16 protrusions/$cm^2$ or greater.

Each recess has, in a side surface thereof, a securing groove for holding the stick-on tissue reinforcement material therein.

Providing grooves opposing each other on the side surfaces of each recess and inserting the stick-on tissue reinforcement material into the grooves can prevent the stick-on tissue reinforcement material from falling off. The stick-on tissue reinforcement material held in the securing grooves is released from the securing grooves by the force of fitting the surgical stapler into the recesses. To reliably release the tissue reinforcement material upon fitting the surgical stapler into the recesses while preventing the stick-on tissue reinforcement material from falling off, the distance between the ends of the two securing grooves is preferably greater than the width of the stick-on tissue reinforcement material by 0.5 mm or greater and 2 mm or less, more preferably 0.5 mm or greater and 1.5 mm or less.

Preferably, each recess becomes wider toward the proximal side of the surgical stapler.

When each recess has a V-shaped structure that becomes wider toward the proximal side of the surgical stapler, the surgical stapler can be easily guided to the recesses. Moreover, in the case that the bottom of the recesses is connected to another portion via bottom-holding grooves as described in detail later, the bottom of the recesses can be more easily withdrawn in releasing the surgical stapler.

The degree of widening of each recess, in other words, the difference between the width at the proximal end and the width at the distal end of each recess, is preferably 0.1 mm or greater, more preferably 0.4 mm or greater while preferably 0.6 mm or less, more preferably 0.3 mm or less, from the standpoint of easier guiding of the surgical stapler to the recesses and the standpoint of the handleability.

Preferably, the bottom of the recesses has an opening in a portion that is to contact the tip of the surgical stapler.

Surgical staplers come in various tip shapes, some with a hook-like curved tip. In fitting such a surgical stapler with a hook-like tip shape into the recesses, the tip may contact the bottom of the recesses before the fitting is complete, leading to insufficient application of the stick-on tissue reinforcement material. When the bottom of the recesses has an opening in a portion that is to contact the tip of the surgical stapler, the opening prevents the tip from interfering with the bottom of the recesses, allowing the stick-on tissue reinforcement material to be reliably applied even when the surgical stapler has a hook-like tip shape. The opening may have any size and shape as long as a surgical stapler with a hook-like tip shape can sufficiently fit into the recesses.

Preferably, the bottom of the recesses protrudes beyond the side surfaces at the proximal end.

When the bottom of the recesses protrudes beyond the side surfaces of the recesses at the proximal end such that the protruding bottom is not continuous with another portion, the surgical stapler can be fitted into the recesses with a stronger force. The protruding length of the bottom of the recesses is preferably 1.0 mm or greater, more preferably 2.0 mm or greater while preferably 10.0 mm or less, more preferably 5.0 mm or less.

The recesses preferably have a bottom thickness of 3 mm or greater and 8 mm or less.

When the bottom thickness of the recesses is within the range, the surgical stapler can be more reliably fitted into the recesses. The bottom thickness of the recesses is more preferably 4 mm or greater and 6 mm or less. The "bottom thickness of the recesses" refers to the thickness including the protrusions, in other words, the thickness from the tips of the protrusions of one recess to the tips of the protrusions of the other recess.

In the tissue reinforcement material applicator of the present invention, the bottom of the recesses is preferably different in material from another portion.

When the bottom of the recesses is different in material from another portion, the protrusions can have a hardness to easily bend when the surgical stapler is fitted into the recesses while the entire tissue reinforcement material applicator has increased strength.

When the bottom of the recesses is different in material from the other portion, the bottom of the recesses is preferably mounted and held in the other portion via bottom-holding grooves provided in the other portion. With such a structure, the application of the stick-on tissue reinforcement material and the release of the surgical stapler can be performed by fitting the surgical stapler into the recesses and then withdrawing the bottom of the recesses. This allows quicker application of the stick-on tissue reinforcement material.

When the bottom of the recesses is mounted in the other portion via the bottom-holding grooves, the bottom-holding grooves preferably become wider toward the proximal side. When the bottom-holding grooves become wider toward the proximal side, the bottom of the recesses can be more easily withdrawn, which allows quicker application of the stick-on tissue reinforcement material.

From the standpoint of balance between the bottom-holding properties and ease of withdrawal, the difference between the width at the distal end and the width at the proximal end of each bottom-holding groove is preferably 0.1 mm or greater, more preferably 0.3 mm or greater while preferably 0.5 mm or less, more preferably 0.4 mm or less.

When the bottom of the recesses is the same in material as the other portion, the periphery of the tissue reinforcement material applicator preferably has a thickness of 5.0 mm or greater and 10.0 mm or less.

When the thickness of the periphery is within the range, bending deformation is less likely to occur during handling of the tissue reinforcement material applicator, so that the stick-on tissue reinforcement material can be more reliably held. When the bottom of the recesses is different in material from the other portion, there is no limitation on the material for forming the periphery, and thus any appropriate thickness according to the material can be selected. The "periphery" herein means a portion constituting the tissue reinforcement material applicator (member) other than the bottom of the recesses.

In the tissue reinforcement material applicator of the present invention, at the end of the member that is continuous with the recesses, the portions on both sides of the recesses preferably protrude beyond the ends of the recesses.

When the portions (periphery) on both sides of the recesses protrude beyond the ends of the recesses at the end (proximal end) that is continuous with the outside of the recesses, in other words, when the ends of the periphery protrude beyond the ends of the recesses at the proximal end of the tissue reinforcement material applicator such that the tissue reinforcement material applicator has a recessed proximal end, the protruding portions (periphery) on both sides of the recesses function as guides for the surgical stapler, allowing the stick-on tissue reinforcement material to be more reliably applied to a predetermined position on the surgical stapler. The protruding length of the portions on both sides of the recesses (protruding length of the periphery) is not limited but is preferably 10 mm or greater and 50 mm or less from the standpoint of surgical stapler guiding properties and handleability.

Preferably, the tissue reinforcement material applicator of the present invention includes guide walls along both long sides of each recess.

Providing guide walls along each recess on both sides of the recess further facilitates guiding of the surgical stapler to the recesses, thus facilitating fitting of the surgical stapler into the recesses.

Each guide wall preferably has an inner surface inclined downward toward the bottom of the recesses (hereinafter a downward-inclined portion of the inner surface of a guide wall is also referred to as an inner-surface inclined portion). When the inner surface of each guide wall is inclined downward toward the bottom of the recesses, the surgical stapler is guided along the inclination toward the bottom of the recesses, thus further facilitating fitting of the surgical stapler into the recesses. The inner-surface inclined portion preferably has an inclination angle of 20° or greater and 40° or less. The inclination angle of the inner-surface inclined portion refers to, in a cross section in the height direction of the guide wall (thickness direction of the tissue reinforcement material applicator), the smaller angle defined by a side corresponding to the inner surface of the guide wall and a perpendicular line drawn from the upper end of the side corresponding to the inner surface of the guide wall to the lower side. Herein, "down" means a direction toward the bottom of the recesses in the thickness direction of the tissue reinforcement material applicator, and "up" refers to a direction opposite thereto. Herein, "inner" means a direction toward the recesses, and "outer" means a direction opposite thereto.

Each guide wall preferably has a height of 1 mm or greater, more preferably 2 mm or greater while preferably 7 mm or less, more preferably 4 mm or less, from the standpoint of handleability and easier fitting of the surgical stapler into the recesses. To more easily fit the surgical stapler into the recesses and further prevent the surgical stapler from getting stuck, the length of each guide wall from the end of the recess on the distal side (distal end) is preferably 20% or greater, more preferably 40% or greater while preferably 80% or less, more preferably 60% or less of the length of the recess.

Preferably, an end of each guide wall on the proximal side of the surgical stapler is inclined downward toward the proximal side (hereinafter, a downward-inclined portion of a proximal end of a guide wall is referred to as a proximal inclined portion).

When the proximal end of each guide wall is inclined downward, the surgical stapler is less likely to get stuck when the tissue reinforcement material applicator is clamped from the proximal side, so that the surgical stapler can be more smoothly guided to the tissue reinforcement material applicator. From the standpoint of more smooth guiding of the surgical stapler, the proximal inclined portion preferably has an inclination angle of 30° or greater and 50° or less. From a similar standpoint, the proximal inclined portion preferably constitutes 2% or greater, more preferably 5% or greater while preferably 30% or less, more preferably 20% or less of the entire guide wall. Herein, the inclination angle of the proximal inclined portion refers to the smaller angle defined by, in an outer surface of the guide wall, the upper side of the proximal inclined portion and a perpendicular line drawn from the distal end of the upper side of the proximal inclined portion to the lower side.

Preferably, the tissue reinforcement material applicator of the present invention includes a grip at an end thereof on the distal side of the surgical stapler.

Providing a grip to the tissue reinforcement material applicator facilitates operations and also prevents the hand from getting wet in immersing the tissue reinforcement material applicator in an aqueous solution.

The grip may have any shape that is easy to hold with fingers, but preferably has a recessed side surface in the longitudinal direction of the recesses. A grip with such a structure makes the tissue reinforcement material applicator easier to hold with fingers and also less slippery. Further, the grip more preferably has an anti-slip rib on a side surface in the longitudinal direction of the recesses. Providing an anti-slip rib on the grip can further prevent fingers from slipping.

Preferably, the grip has a cut-out in a side surface on the side of the recesses.

Providing a cut-out in the side surface of the grip on the side of the recesses can reduce or prevent the interference of the tip of the surgical stapler with the grip, thus further facilitating fitting of the surgical stapler into the recesses. The cut-out may have any shape and size as long as the tip of the surgical stapler does not interfere. Examples of the shape include a semi-spherical shape and a rectangular shape.

The material of the member, in other words, the material of the tissue reinforcement material applicator of the present invention, is not limited, but the material preferably has a hardness that allows the protrusions to bend when the surgical stapler is fitted into the recesses. Examples of such a material include silicone rubber, urethane rubber, and polyolefin elastomer. In particular, when the tissue reinforcement material applicator is sterilized and packaged with the stick-on reinforcement material held therein in the manufacturing process, silicone rubber, which is highly durable, is preferred because in such a case heat resistance and dimensional stability are required. When the bottom of the recesses is made of a different material from the other portion, the material of the bottom of the recesses is preferably the above material, and the material of the other portion preferably is preferably polyethylene or polypropylene from the standpoint of strength, ease of molding, and other properties.

The tissue reinforcement material applicator of the present invention may be produced using any method. When the bottom of the recesses is made of the same material as the other portion, the tissue reinforcement material applicator may be produced by injection molding, press molding, or cutting, for example. When the bottom of the recesses is made of a different material from the other portion, for example, the tissue reinforcement material applicator is produced by producing a U-shaped housing including the securing grooves and the bottom-holding grooves and a platform including the bottom of the recesses with brush-like protrusions and fittable portions, which correspond to the bottom-holding grooves, along the side surfaces of the bottom, and then fitting the platform into the bottom-holding grooves. The housing and platform can be produced by injection molding, press molding, cutting, or other methods.

The stick-on tissue reinforcement material may be held in the tissue reinforcement material applicator of the present invention in the surgical field, but the tissue reinforcement material applicator may be sterilized, packaged, transferred, and stored with the stick-on tissue reinforcement material held therein to improve the handleability of the stick-on tissue reinforcement material and simplify the operations in the surgical field.

The present invention also encompasses a tissue reinforcement material application kit including the tissue reinforcement material applicator of the present invention and the stick-on tissue reinforcement material held in the securing grooves of the tissue reinforcement material applicator.

Preferably, the tissue reinforcement material application kit of the present invention includes a cap at an end thereof on the proximal side of the surgical stapler.

Protecting the end of the tissue reinforcement material application kit on the proximal side of the surgical stapler can reduce or prevent falling of the stick-on tissue reinforcement material during transfer or storage. The cap may have any shape appropriately determined according to the shape of the end of the tissue reinforcement material applicator on the proximal side of the surgical stapler. The cap is removed in the surgical field before the tissue reinforcement material application kit is immersed in an aqueous solution.

Hereinbelow, embodiments and usage of the tissue reinforcement material applicator of the present invention are described referring to drawings. FIG. 1 is a schematic view of an example of the tissue reinforcement material applicator of the present invention. FIG. 1 and FIGS. 2 and 3 (described later) each show the distal side in the right background of the figure and the proximal side on the left foreground. FIG. 1 shows an example of a tissue reinforcement material applicator in which the bottom (platform) of the recesses is made of a different material from another portion (housing). As shown in FIG. 1, a tissue reinforcement material applicator 1 of the present invention has recesses 2 opposing each other on both surfaces of a plate-shaped member. The two recesses 2 have brush-like protrusions 3 on the bottom surfaces thereof. The recesses 2 have, in their side surfaces, securing grooves 4 for holding a stick-on tissue reinforcement material 5. The stick-on tissue reinforcement material 5 is inserted into and held in the securing grooves 4. The two recesses 2 are continuous with the same edge (same side surface) of the member (tissue reinforcement material applicator 1), and therefore when a surgical stapler is fitted from the end (open end) of the tissue reinforcement material applicator 1 with which the recesses 2 are continuous such that the surgical stapler completely engages with the recesses 2, two pieces of the stick-on tissue reinforcement material can be simultaneously precisely applied to predetermined positions of the surgical stapler. At the proximal end of the tissue reinforcement applicator 1, when the ends of the periphery (portion constituting the member other than the bottom of the recesses 2) protrude beyond the ends of the recesses 2, the projecting portions function as guides to the recesses 2, further facilitating fitting of the surgical stapler into the recesses. When the bottom of the recesses 2 has an opening 6 in a portion that is to contact a tip of a surgical stapler, the opening 6 accommodates the tip in fitting the surgical stapler into the recesses, so that even a surgical stapler with a hook-like tip can be completely fitted into the tissue reinforcement material applicator. In FIG. 1, the grooves between the two pairs of securing grooves 4 are grooves (bottom-holding groove 7) for fitting the bottom (platform) of the recesses.

FIG. 2 is a schematic view of the tissue reinforcement material applicator of the present invention in a use state. As shown in FIG. 2, the tissue reinforcement material applicator 1 of the present invention is used in the following manner: first, the stick-on tissue reinforcement material 5 is held in the securing grooves 4 of the two recesses. The operation of holding the stick-on tissue reinforcement material 5 may be performed in the surgical field, or the stick-on tissue reinforcement material 5 may be held in the tissue reinforcement material applicator 1 in the manufacturing process and sterilized, packaged, and transferred. Next, the stick-on tissue reinforcement material 5 together with the tissue reinforcement material applicator 1 is immersed in an aqueous solution such as sterilized water, saline, or a buffer solution. The tissue reinforcement material applicator 1 with the stick-on tissue reinforcement material 5 is then taken out from the aqueous solution such as sterilized water, saline, or a buffer solution. A surgical stapler 8 is inserted from the end (open end) with which the recesses are continuous, and the recesses are clamped between the jaws of the surgical stapler, whereby two pieces of the stick-on tissue reinforcement material 5 are simultaneously applied to the surgical stapler 8. At this time, the protrusions around the proximal portion of the surgical stapler 8, which contacts the stick-on tissue reinforcement material 5 first, bend as the clamping proceeds, allowing the surgical stapler 8 to fit into the recesses until the distal portion, which contacts the tissue reinforcement material later, is sufficiently in contact with and pressed against the stick-on tissue reinforcement material 5. As a result, application failure such as lifting or peeling can be reduced or prevented throughout the entire surface of the stick-on tissue reinforcement material 5. Even in the case of the surgical stapler 8 with a hook-like tip as shown in FIG. 2, the opening 6 in the portion that is to contact the tip in fitting the surgical stapler 8 into the recesses accommodates the tip, so that the surgical stapler 8 can be completely fitted. In the case of the tissue reinforcement material applicator 1 including the platform and the housing as shown in FIG. 1, the surgical stapler 8 can be removed from the tissue reinforcement material applicator 1 by withdrawing the platform toward the proximal side with the surgical stapler 8 being fitted in the recesses after fitting the surgical stapler 8 into the recesses.

FIG. 3 is a schematic view of an example of the tissue reinforcement material applicator of the present invention. The embodiment shown in FIG. 3 includes the embodiment shown in FIG. 1 and further includes a grip 9 at the distal end. The grip 9 prevents fingers from getting wet when the tissue reinforcement material applicator 1 is immersed in the aqueous solution, and also facilitates the immersing operation. When the grip 9 has a side surface recessed at the center, the tissue reinforcement material applicator 1 is easier to hold with fingers. When the grip 9 further has an anti-slip rib on a side surface, the tissue reinforcement material applicator 1 is easier to hold. When the bottom of the recesses 2 protrudes beyond the side surfaces at the proximal end of the recesses 2, the surgical stapler can be fitted into the recesses with a stronger force. When the grip 9 further has a cut-out 11 in the side surface on the side of the recesses 2, the tip of the surgical stapler is less likely to interfere with the grip 9 when the surgical stapler is fitted into the recesses, so that lifting of the stick-on tissue reinforcement material at the tip can be further reduced or prevented.

In the embodiment of FIG. 3, the protrusions 3 become shorter from the distal side toward the proximal ends of the recesses 2. When the protrusions 3 become shorter toward the proximal side, the bottom of the recesses 2 is inclined, so that the stick-on tissue reinforcement material can be more reliably clamped from the proximal side to the tip with a clamping action of the surgical stapler, while the stick-on tissue reinforcement material contacts the surgical stapler to the tip with a strong force owing to the resilience (elasticity)

of the protrusions. As a result, lifting or peeling of the stick-on tissue reinforcement material at the tip can be reduced or prevented.

In the embodiment of FIG. 3, each recess 2 has guide walls 10 along the recess on both sides of the recess. The guide walls 10 guide the surgical stapler to the recesses 2, further facilitating fitting of the surgical stapler into the recesses. When each guide wall 10 has a proximal end inclined downward toward the proximal side, the surgical stapler is less likely to get stuck, further facilitating fitting of the surgical stapler into the recesses. When each guide wall 10 has an inner surface inclined downward toward the bottom of the recesses 2, the surgical stapler is guided along the inclination to the bottom of the recesses, even further facilitating fitting of the surgical stapler into the recesses.

In the embodiment of FIG. 3, the bottom of the recesses 2 becomes wider toward the proximal side of the surgical stapler. In other words, the housing becomes wider toward the proximal side. Such a structure allows the surgical stapler to more easily enter the recesses.

In the embodiment of FIG. 3, the width between the bottom-holding grooves 7 for fitting the platform increases toward the proximal side. Such bottom-holding grooves 7 allow the platform to be easily withdrawn with the surgical stapler being still fitted into the recesses. The surgical stapler thus can be easily removed, leading to easier and quicker application of the stick-on tissue reinforcement material 5 to the surgical stapler.

As shown in FIG. 3, when the stick-on tissue reinforcement material 5 is held in the tissue reinforcement material applicator 1 in advance to provide a tissue reinforcement material application kit, the tissue reinforcement material application kit preferably includes a cap 12. Protecting the proximal end of the tissue reinforcement material reinforcement kit with the cap 12 can reduce or prevent unintended falling of the stick-on tissue reinforcement material during transfer or storage. The cap 12 is removed when the tissue reinforcement material applicator 1 is immersed in an aqueous solution.

Next, the stick-on tissue reinforcement material used in combination with the tissue reinforcement material applicator of the present invention is described.

The stick-on tissue reinforcement material means a tissue reinforcement material to be secured to a surgical stapler with adhesion. The stick-on tissue reinforcement material may be any adhesive tissue reinforcement material such as a conventional tissue reinforcement material with an adhesive substance applied thereto or with an adhesive substance layer laminated thereon or a self-adhesive tissue reinforcement material, but is preferably a stick-on tissue reinforcement material including a fabric layer containing a bioabsorbable material and a sponge layer containing a water-soluble polymer, the fabric layer and the sponge layer being integrally laminated. With such a stick-on tissue reinforcement material, the effects of the present invention are greatly exhibited. In the following, a stick-on tissue reinforcement material including a fabric layer containing a bioabsorbable material and a sponge layer containing a water-soluble polymer, the fabric layer and the sponge layer being integrally laminated, is described.

The fabric layer functions as a tissue reinforcement material. The fabric layer, containing a bioabsorbable material, is highly safe as it is eventually absorbed in the living body after reinforcement is no longer needed and thereby prevents foreign matter from staying in the body for a long time. The sponge layer functions to impart adhesion to the stick-on tissue reinforcement material. The water-soluble polymer exhibits adhesion when absorbing moisture. Herein, "sponge" refers to a structure containing many voids.

Herein, "integrally laminated" means that the fabric layer and the sponge layer are joined together to the extent that the two layers are less likely to separate even when a force is applied thereto. The fabric layer and the sponge layer are integrally laminated, for example, by floating the fabric on a water-soluble polymer solution, which is a raw material of the sponge layer, and performing freeze-drying. To enhance the interfacial adhesion between the fabric layer and the sponge layer, the fabric is preferably hydrophilized using a plasma treatment device or the like so that it can have improved permeability to the water-soluble polymer solution.

Examples of the bioabsorbable material include synthetic absorbable polymers, for example, α-hydroxy acid polymers such as polyglycolide, polylactide (D, L, or DL), glycolide-lactide (D, L, or DL) copolymers, glycolide-ε-caprolactone copolymers, lactide (D, L, or DL)-ε-caprolactone copolymers, poly(p-dioxanone), and glycolide-lactide (D, L, or DL)-ε-caprolactone copolymers, and natural absorbable polymers such as collagen, gelatin, chitosan, and chitin. These may be used alone or in combination of two or more thereof. For example, the bioabsorbable material may be a combination of a synthetic absorbable polymer and a natural absorbable polymer. In particular, the bioabsorbable material is preferably polyglycolic acid, polylactic acid, or a copolymer of lactic acid and caprolactone because these exhibit high strength.

When the bioabsorbable material used is polyglycolide (homopolymer or copolymer of glycolide), the lower limit of the weight average molecular weight of the polyglycolide is preferably 30,000 and the upper limit thereof is preferably 1,000,000. Polyglycolide having a weight average molecular weight of 30,000 or more can more securely reinforce tissue. Polyglycolide having a weight average molecular weight of 1,000,000 or less can further reduce or prevent foreign body reaction. The lower limit of the weight average molecular weight of the polyglycolide is more preferably 50,000 and the upper limit thereof is more preferably 300,000.

The fabric layer may be in any form. For example, the fabric layer may be in the form of a knitted fabric, a woven fabric, a nonwoven fabric, or a film. In particular, the fabric layer is preferably a nonwoven fabric from the standpoint of flexibility, air permeability, and ease of staple penetration.

The nonwoven fabric used as the fabric layer may have any areal weight. The lower limit thereof is preferably 3 $g/m^2$ and the upper limit thereof is preferably 300 $g/m^2$. The nonwoven fabric having an areal weight of 3 $g/m^2$ or more can more securely reinforce tissue. A nonwoven fabric having an areal weight of 300 $g/m^2$ or less can further increase adhesion to tissue. The lower limit of the areal weight of the bioabsorbable nonwoven fabric is more preferably 5 $g/m^2$ and the upper limit thereof is more preferably 100 $g/m^2$.

The nonwoven fabric may be produced using any conventionally known method such as electrospinning deposition, melt blowing, needle punching, spunbonding, flash spinning, hydroentanglement, air-laid methods, thermal bonding, resin bonding, or wet methods.

Examples of the water-soluble polymer include natural polymers such as polysaccharide materials and protein materials and synthetic polymers such as polyacrylic acid and polyvinyl alcohol. Tissue reinforcement materials for surgical staplers require highly biocompatible materials because they are embedded in the body. In particular, the water-soluble polymer is preferably a polysaccharide material or a protein material because these materials are less likely to be displaced during operation of the surgical stapler and have adhesion to a degree that allows easy separation after stapling. Examples of the polysaccharide material include hydroxypropyl methylcellulose, pullulan, sodium alginate, and carboxymethylcellulose. Examples of the protein material include gelatin, collagen peptide, and water-soluble elastin.

The water-soluble polymer preferably has a viscosity of 1 mPa·s or higher and 500 mPa·s or lower when in the form of a 2% concentration aqueous solution. A water-soluble polymer having a viscosity within the range can form an appropriately soft sponge layer that exhibits appropriate adhesion after moisture permeates it. Such a sponge layer makes it easy to bond the reinforcement material to a surgical stapler.

The sponge layer is preferably a freeze-dried product.

Freeze-drying can form a sponge layer without a pore-forming agent, eliminating the need for removal of a pore-forming agent and resulting in a sponge layer with high material purity. The freeze-drying may be performed using any conventionally known method.

The sponge layer preferably has a thickness of 0.3 mm or more and 3.0 mm or less.

A sponge layer having a thickness in the range can further reduce or prevent displacement during operation of the surgical stapler, and can be easily adjusted to have an appropriate adhesion that allows easy separation after stapling. The thickness of the sponge layer is more preferably 0.3 mm or more and 0.5 mm or less. The thickness of the sponge layer formed by freeze-drying can be adjusted by adjusting the amount of the water-soluble polymer solution with which the fabric layer is soaked. The thickness of the sponge layer herein refers to the average of thicknesses measured across the entire area of the sponge layer using a dial indicator (e.g., SMD-565J-L, produced by Teclock Co., Ltd.) at intervals of one site/$cm^2$.

The sponge layer may have any density, but preferably has a density of 0.1 $g/cm^3$ or higher and 0.7 $g/cm^3$ or lower.

A sponge layer having a density within the range can further reduce or prevent displacement during operation of the surgical stapler, and can be easily adjusted to have an appropriate adhesion that allows easy separation after stapling.

The stick-on tissue reinforcement material has a shape corresponding to the portion of the surgical stapler to which the stick-on tissue reinforcement material is to be applied.

Since the stick-on tissue reinforcement material is applied to the surgical stapler by bonding, it does not need to be tubular to be secured to a surgical stapler like conventional reinforcement materials. As a result, the reinforcement material is not only less likely to get caught when inserted into a port, but also hardly changes the diameter of the surgical stapler when applied thereto, so that the surgical stapler can pass through a narrower port.

The stick-on tissue reinforcement material of the present invention preferably has an adhesion strength of 5 $N/cm^2$ or higher when bonded to a surgical stapler.

An adhesion strength within the range when the stick-on tissue reinforcement material is bonded to a surgical stapler can further reduce or prevent displacement during operation of the surgical stapler. The adhesion strength is more preferably 10 $N/cm^2$ or higher. The upper limit of the adhesion strength is not limited, but is preferably 30 $N/cm^2$ or lower for easy separation after stapling. The adhesion strength can be specifically measured by the following method.

The stick-on tissue reinforcement material is cut into a size of 8 mm in width×40 mm in length. Only a length of 10 mm is bonded to a working surface (anvil side) of a surgical stapler (e.g., Endopath Stapler ECHELON FLEX 60, produced by Ethicon, Inc.) presoaked with saline, and pressed for three minutes so that the stick-on tissue reinforcement material is adhered to the working surface. Subsequently, the handle of the surgical stapler is attached to the lower chuck of a tensile tester (e.g., Autograph Precision Universal Tester AG-X Plus, produced by Shimadzu Corporation), and the end of the stick-on tissue reinforcement material protruding from the surgical stapler is attached to the upper chuck of the tensile tester. Thereafter, a tensile test is performed at a pulling speed of 100 mm/min, and the maximum load at which displacement occurs is defined as the adhesion strength.

The stick-on tissue reinforcement material of the present invention may be produced using any method. For example, the reinforcement material may be produced using the above method, or may be produced by placing the fabric on the bottom surface, pouring the water-soluble polymer solution onto the fabric after ensuring that the water-soluble polymer solution does not flow to the lower surface of the fabric, and performing freeze-drying to form a sponge layer.

Advantageous Effects of Invention

The present invention can provide a tissue reinforcement material applicator that enables quick, precise, and easy application of a stick-on tissue reinforcement material to a surgical stapler with less application failure, and a tissue reinforcement material application kit including the tissue reinforcement material applicator.

DESCRIPTION OF EMBODIMENTS

Embodiments of the present invention are described in more detail below with reference to drawings. The present invention should not be limited to these embodiments.

Example 1

(1) Production of Stick-on Tissue Reinforcement Material

Distilled water was added to hydroxypropyl methylcellulose (HPMC) (viscosity grade 6: AN6, 2% solution viscosity: 5.1 mPa/s, produced by Mitsubishi-Chemical Foods Corporation) to give an 8% by weight HPMC aqueous solution. Subsequently, 10 g of the HPMC aqueous solution was added to a petri dish (0100 mm). Next, a polyglycolic acid (PGA) nonwoven fabric sheet cut into 0100 mm as a fabric layer was floated on the HPMC aqueous solution in the petri dish. After confirming that the HPMC aqueous solution permeated the nonwoven fabric sheet, the petri dish was put in a freezer at −80° C. for 15 minutes, whereby the HPMC aqueous solution was frozen. Thereafter, the frozen HPMC aqueous solution was dried by a vacuum freeze dryer to form a HPMC sponge layer (adhesive layer) on the nonwoven fabric, whereby a stick-on tissue reinforcement material was prepared.

Figure 1:
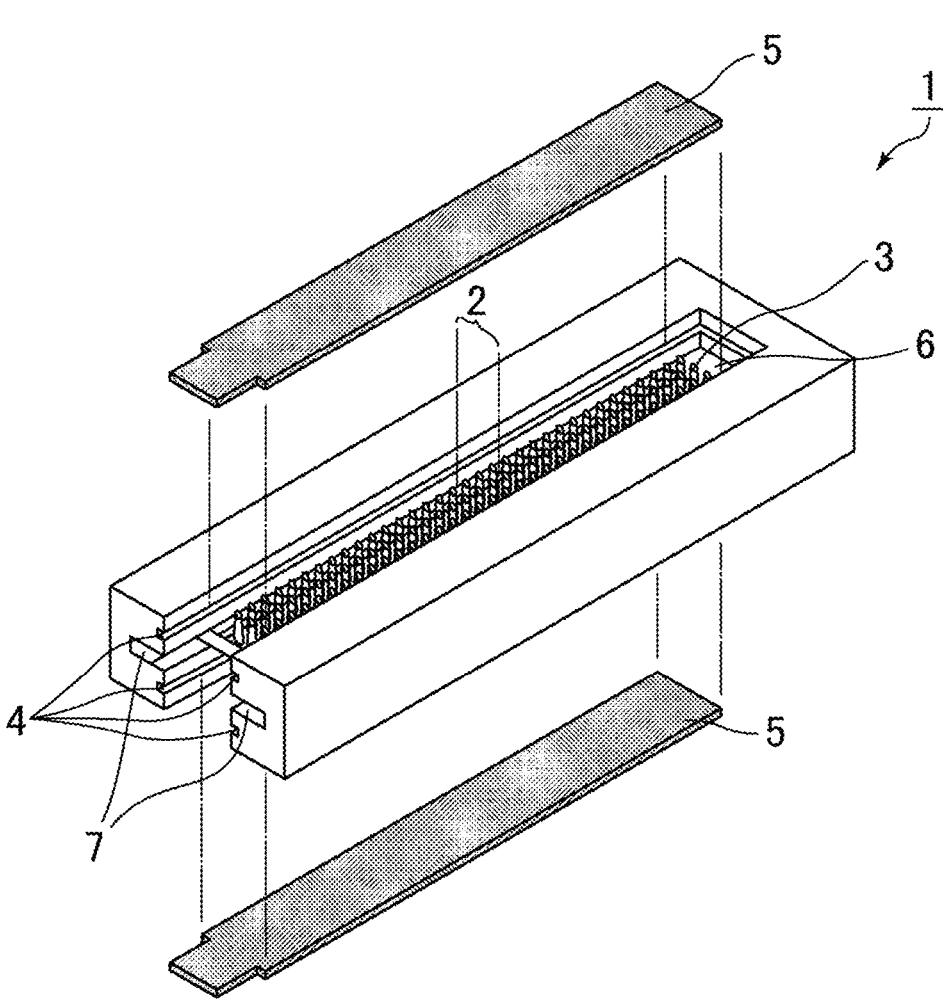
FIG. 1 is a schematic view of an example of the tissue reinforcement material applicator of the present invention.

(2) Production of Tissue Reinforcement Material Applicator and Stick-on Tissue Reinforcement Material Application Kit Polyethylene was injection-molded into a U-shaped housing with two pairs of securing grooves and one platform-fitting groove as shown in FIG. 1. Each securing groove had a width of 0.5 mm. Each bottom-holding groove had a width of 3.5 mm. The dimensions inside the U-shape were as follows: 11 mm in height×9 mm in width×70 mm in length. Separately, silicone (produced by Wacker Asahikasei Silicone Co., Ltd., SILPURAN® 8020/40) was injection-molded into a platform. The platform had a bottom (9 mm in width×60 mm in length) of recesses having brush-like protrusions with a length of 2 mm at a density of 16 protrusions/cm² on both surfaces, and had margines (flat portions) with a width of 3.5 mm along both long sides of the bottom for fitting into the bottom-holding grooves. Next, the obtained platform was fitted into the bottom-holding grooves of the obtained housing to give a tissue reinforcement material applicator. At this time, the platform was inserted until it reached the position 60 mm from the end (insertion end) of the housing, thereby providing an opening with a size of 9 mm in width×10 mm in length on the closed end of the housing.

The obtained stick-on tissue reinforcement material was cut into a size of 10 mm in width×60 mm in length and held in the securing grooves with the adhesive layer facing up, whereby a tissue reinforcement material application kit was obtained.

(3) Application to Surgical Stapler

Figure 2:
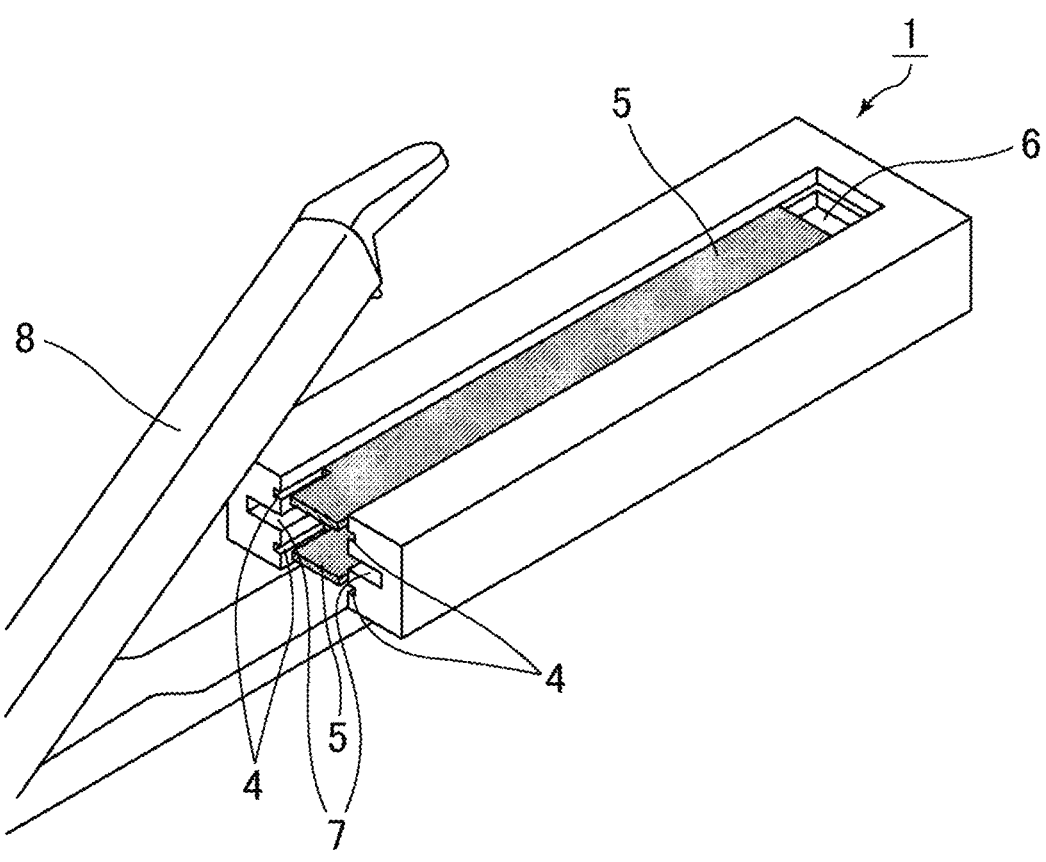
FIG. 2 is a schematic view of the tissue reinforcement material applicator of the present invention in a use state.

The obtained stick-on tissue reinforcement material application kit was immersed in saline (OTSUKA NORMAL SALINE, produced by Otsuka Pharmaceutical Co., Ltd.) for five seconds. Then, as shown in FIG. 2, a surgical stapler (produced by Ethicon, Inc., Endopath Stapler ECHELON FLEX 60) was inserted from the open end of the housing, and the portion between the recesses was clamped between the jaws of the surgical stapler for five seconds. Then, with the surgical stapler being fitted into the recesses, the platform was withdrawn from the housing to release the surgical stapler from the tissue reinforcement material applicator. The portions of the surgical stapler to which the tissue reinforcement material was applied were inspected. The stick-on tissue reinforcement material was completely applied to the surgical stapler to the tip without displacement from the predetermined positions. The time from the immersion into saline to the completion of the application was about 20 seconds.

Example 2

Figure 3:
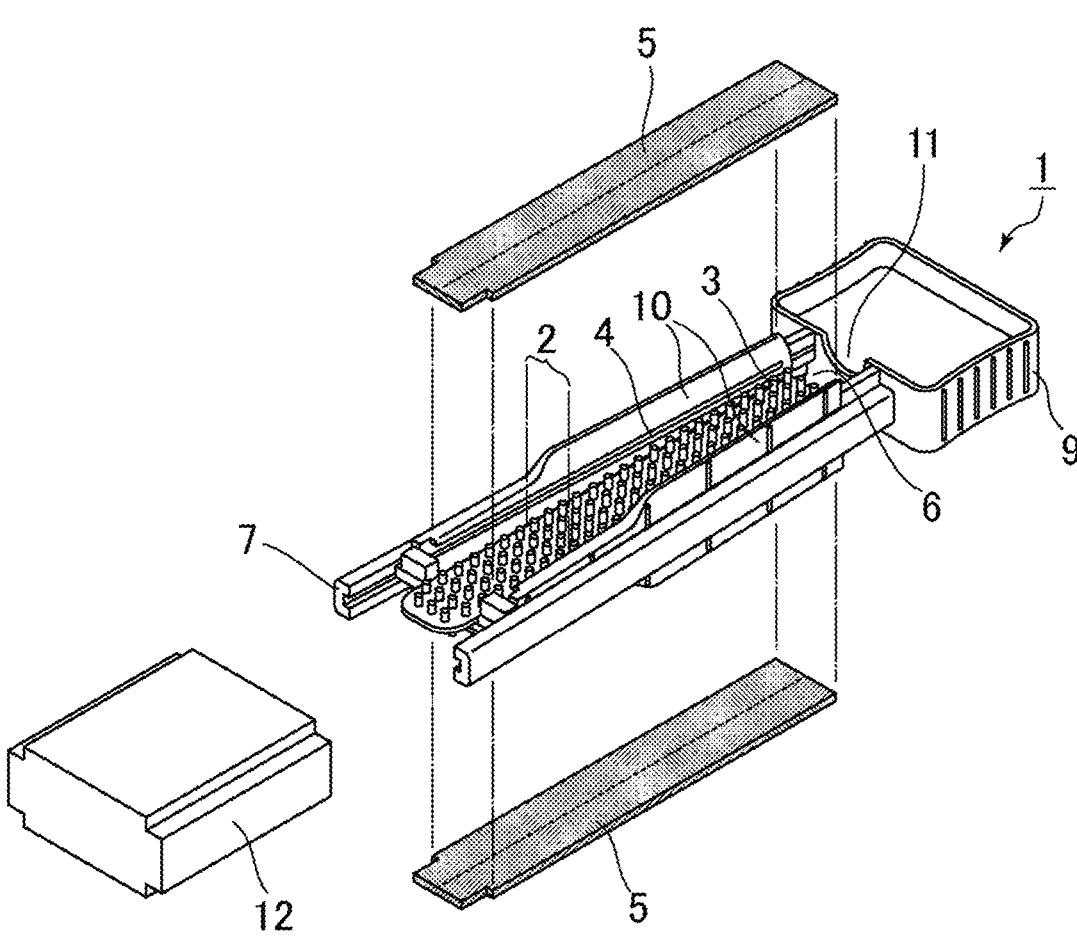
FIG. 3 is a schematic view of an example of the tissue reinforcement material application kit of the present invention.

Polypropylene was injection-molded into a U-shaped housing with a grip, two pairs of securing grooves, one pair of bottom-holding grooves, and two pairs of guide walls as shown in FIG. 3. Each securing groove had a width of 0.5 mm. Each bottom-holding groove had a length in the thickness direction of 2 mm at the distal end and 2.4 mm at the proximal end. The width inside the U-shape including the portions constituting the securing grooves and the guide walls was 17 mm at the distal end and 17.4 mm at the proximal end, so that the housing became wider toward the proximal side. Each guide wall had a height of 2 mm and a length of 34 mm and had an inner-surface inclined portion with an inclination angle of 30° in the inner surface and a proximal inclined portion with an inclination angle of 30° at the proximal end.

Separately, silicone (produced by Wacker Asahikasei Silicone Co., Ltd., SILPURAN® 8020/40) was injection-molded into a platform. The platform had a bottom (9 mm in width×52 mm in length×1 mm in bottom surface thickness) of recesses having brush-like protrusions with a maximum length of 2.2 mm at a density of 9 protrusions/cm² on both bottom surfaces, and had margines (flat portions) with a width of 3.5 mm along both long sides of the bottom for fitting into the bottom-holding grooves. At this time, the length of the protrusions was changed from 2.2 mm to 1.95 mm to 1.7 mm from the distal side to the proximal side so that the length decreased toward the proximal side. The sections with these lengths each constituted ⅓ of the length of the bottom.

Next, the obtained platform was inserted into the bottom-holding grooves of the obtained housing to give a tissue reinforcement material applicator. At this time, an opening with a size of about 9 mm in width×10 mm in length was provided on the distal side of the recesses. The obtained stick-on tissue reinforcement material was cut into a size of 10 mm in width×60 mm in length and held in the securing grooves with the adhesive layer facing up, whereby a tissue reinforcement material application kit was obtained.

The tissue reinforcement material application kit was operated as in Example 1 to apply the stick-on tissue reinforcement material to the surgical stapler. The stick-on tissue reinforcement material was completely applied to the surgical stapler to the tip without displacement from the predetermined positions. The time from the immersion into saline to the completion of the application was about 15 seconds.

Comparative Example 1

The stick-on tissue reinforcement material prepared in Example 1 was cut to fit the shape of the surgical stapler. The stick-on tissue reinforcement material was then immersed in saline for five seconds and bonded to predetermined positions (two positions) of the surgical stapler by pressing the material on the positions for five seconds using a polyethylene foam sheet with a thickness of 2 mm. The stick-on tissue reinforcement material was applied without displacement from the predetermined positions, but the time from the immersion in saline to the completion of the application was about 90 seconds.

Comparative Example 2

A stick-on tissue reinforcement material application kit was produced as in Example 1 except that it had no brush-like protrusions, and the stick-on tissue reinforcement material was applied to a surgical stapler. The time from the immersion in saline to the completion of the application was the same as in Example 1, and the tissue reinforcement material was applied without displacement from the predetermined positions, but lifting occurred at part of the tip.

INDUSTRIAL APPLICABILITY

The present invention can provide a tissue reinforcement material applicator that enables quick, precise, and easy application of a stick-on tissue reinforcement material to a surgical stapler with less application failure, and a tissue reinforcement material application kit including the tissue reinforcement material applicator.

REFERENCE SIGNS LIST

1 tissue reinforcement material applicator
2 recess
3 protrusion
4 securing groove
5 stick-on tissue reinforcement material
6 opening
7 bottom-holding groove
8 surgical stapler
9 grip
10 guide wall
11 cut-out
12 cap

The invention claimed is:

1. A tissue reinforcement material applicator for securing a stick-on tissue reinforcement material to a surgical stapler, the tissue reinforcement material applicator comprising a plate-shaped member,
 the tissue reinforcement material applicator having recesses opposing each other on both surfaces of the plate-shaped member,
 each recess having a shape corresponding to a shape of a portion of the surgical stapler to which the stick-on tissue reinforcement material is to be applied,
 each recess being continuous with the same edge of the plate-shaped member,
 each recess having brush-like protrusions on a bottom surface thereof,
 each recess having, in a side surface thereof, a securing groove for holding the stick-on tissue reinforcement material therein.

2. The tissue reinforcement material applicator according to claim 1,
 wherein a bottom of the recesses is different in material from another portion.

3. The tissue reinforcement material applicator according to claim 1,
 wherein a bottom of the recesses has an opening in a portion that is to contact a tip of the surgical stapler.

4. The tissue reinforcement material applicator according to claim 1,
 wherein the brush-like protrusions have a density of 9 protrusions/cm² or greater and 25 protrusions/cm² or less.

5. The tissue reinforcement material applicator according to claim 1,
 wherein the brush-like protrusions have a length of 0.5 mm or greater and 5 mm or less.

6. The tissue reinforcement material applicator according to claim 1,
 wherein the brush-like protrusions become shorter toward ends of the recesses, the ends being on a proximal side of the surgical stapler.

7. The tissue reinforcement material applicator according to claim 1,
 wherein each recess becomes wider toward a proximal side of the surgical stapler.

8. The tissue reinforcement material applicator according to claim 1, comprising guide walls along both long sides of each recess.

9. The tissue reinforcement material applicator according to claim 8, wherein each guide wall has an end on a proximal side of the surgical stapler, and the end is inclined downward toward the proximal side.

10. The tissue reinforcement material applicator according to claim 1, comprising a grip at an end thereof on a distal side of the surgical stapler.

11. The tissue reinforcement material applicator according to claim 10, wherein the grip has a cut-out in a side surface on a side of the recesses.

12. A tissue reinforcement material application kit comprising:

the tissue reinforcement material applicator according to claim 1; and the stick-on tissue reinforcement material held in the securing grooves of the tissue reinforcement material applicator.

13. The tissue reinforcement material application kit according to claim 12, comprising a cap at an end thereof on a proximal side of the surgical stapler.

* * * * *